(12) United States Patent
Pohan et al.

(10) Patent No.: US 7,602,881 B2
(45) Date of Patent: Oct. 13, 2009

(54) RADIATION DETECTION UNIT FOR A COMPUTER TOMOGRAPH

(75) Inventors: Claus Pohan, Baiersdorf (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 107 days.

(21) Appl. No.: 11/723,489

(22) Filed: Mar. 20, 2007

(65) Prior Publication Data

US 2007/0286333 A1   Dec. 13, 2007

(30) Foreign Application Priority Data

Mar. 21, 2006   (DE) .................. 10 2006 012 946

(51) Int. Cl.
*A61B 6/03* (2006.01)
(52) U.S. Cl. ............................. 378/19; 378/6
(58) Field of Classification Search ............ 378/6, 378/7, 19, 98.4, 98.8
See application file for complete search history.

(56) References Cited

U.S. PATENT DOCUMENTS

| | | | |
|---|---|---|---|
| 6,046,458 A * | 4/2000 | Rantanen | 378/167 |
| 6,340,436 B1 * | 1/2002 | Yamada et al. | 378/6 |
| 6,925,140 B2 | 8/2005 | Bruder | |
| 2005/0135562 A1 * | 6/2005 | Freund et al. | 378/147 |
| 2005/0147200 A1 * | 7/2005 | Nukui | 378/7 |
| 2006/0011852 A1 * | 1/2006 | El-Hanany et al. | 250/370.09 |
| 2006/0055087 A1 | 3/2006 | Freund et al. | |
| 2006/0171502 A1 | 8/2006 | Schlomka et al. | |

FOREIGN PATENT DOCUMENTS

| | | |
|---|---|---|
| DE | 100 55 739 A1 | 5/2002 |
| DE | 100 11 877 C2 | 8/2002 |
| DE | 102 28 941 A1 | 1/2004 |
| DE | 10 2004 027 158 A1 | 12/2005 |
| WO | WO 9833062 A1 * | 7/1998 |
| WO | WO 2005036147 A1 * | 4/2005 |

* cited by examiner

*Primary Examiner*—Chih-Cheng G Kao
(74) *Attorney, Agent, or Firm*—Harness, Dickey & Pierce, P.L.C.

(57) ABSTRACT

A radiation detection unit is disclosed for a computer tomograph, and a computer tomograph having a radiation detection unit is also disclosed. In at least one embodiment, the radiation detection unit for a computer tomograph includes at least one scattered radiation sensor, set up and arranged to measure scattered radiation.

20 Claims, 3 Drawing Sheets

RADIATION DETECTION UNIT FOR A COMPUTER TOMOGRAPH

PRIORITY STATEMENT

The present application hereby claims priority under 35 U.S.C. §119 on German patent application numbers DE 10 2006 012 946.6 filed Mar. 21, 2006, the entire contents of which is hereby incorporated herein by reference.

FIELD

Embodiments of the invention generally relate to a radiation detection unit for a computer tomograph, and/or to a computer tomograph having such a radiation detection unit.

BACKGROUND

When objects (patient, couch, etc) are being transirradiated in computer tomographs, undesired scattered radiation also is produced in addition to the primary radiation required for image calculation. Owing to the slight extent in a z-direction (corresponding to the direction of the gantry axis of rotation) of previous detectors for radiation measurement, it has sufficed to collimate scattered beams in only one beta direction (corresponding to the direction of the beam fan angle) via suitable collimator plate arrangements. Such collimator arrangements are disclosed, for example, in DE 100 11 877 C2.

With the trend toward ever larger detector surfaces in the z-direction, the collimator arrangements can no longer be designed in a beam-delimiting fashion such that they essentially eliminate scattered radiation. Consequently, the influence of scattered radiation is also no longer negligible in the z-direction and must be suppressed by way of suitable measures.

A theoretically possible, two-dimensional collimation in beta and z-directions by way, for example, of pyramidally arranged collimator plate structures can be implemented technically and economically only with great difficulty because of the requisite aspect ratio of greater than 1:20.

SUMMARY

In at least one embodiment of the present invention, a possibility for suppressing the influence of scattered radiation on the operation of a computer tomograph is provided.

A radiation detection unit of at least one embodiment includes at least one scattered radiation sensor that is set up and arranged for measuring scattered radiation. It is thereby possible to take account of the measured scattered radiation during image calculation without the radiation produced requiring to be inordinately constricted or expensively collimated. This also permits the beam to be spread out further in the z-direction, and thus to permit larger detector surfaces in the z-direction, and this leads to shorter measuring times and therefore to a lesser radiation burden.

A computer tomograph of at least one embodiment that is equipped with at least one such radiation detection unit may also advantageously be provided with or connected to an evaluation unit that uses the measured values output by the at least one scattered radiation sensor for scattered radiation correction during image calculation.

The at least one scattered radiation sensor may advantageously be arranged outside a primary fan beam path, since the scattered radiation component is high there and so a correction of the scattered radiation pattern is simplified. However, it is also possible to arrange a scattered radiation sensor at the edge of the primary fan beam path, for example, and to calculate the component of the primary radiation correspondingly with a higher outlay.

A number of scattered radiation sensors, in at least one embodiment, are provided for the use of inexpensive sensors. For the purpose of simple and reliable evaluation, it is then advantageous, furthermore, when the scattered radiation sensors are arranged in two rows in relation to a gantry rotational axis on both sides of the primary fan beam path. This can be, for example, an arrangement with the same spacing on both sides from the middle of the primary beam, that is to say a +z and −z with reference to the middle of the primary beam. For the purpose of simple and reliable evaluation, it is advantageous, furthermore, when the scattered radiation sensors of a row are arranged at defined spacings (in the beta direction) from one another, in particular at the spacing of a module pitch, in each case.

The scattered radiation sensor may be, for example, a photodiode to which scintillation ceramic has been applied.

It is also advantageous, in at least one embodiment, when the scattered radiation sensor has at least one beam entry slit for introducing the secondary radiation which is set up and arranged accordingly, such that the scattered radiation, (and as far as possible only that) falls through the beam entry slit onto the scintillation ceramic. In order to suppress laterally incident radiation as the scattered radiation, the beam entry slit is formed at least partially by housing parts having radiation absorbing material, or is surrounded by such. In this case, the housing parts can include entirely radiation absorbing material, and this simplifies the production steps; alternatively, the housing parts can have insertion parts made from radiation absorbing material, and this lowers the material costs.

The housing parts may be produced by injection molding for the purposes of simple production. Thus, there is no need for any intricate collimator plates on the scattered radiation sensors, but that the collimation of the scattered radiation can be achieved by way of simple injection molded parts made from absorbing material.

BRIEF DESCRIPTION OF THE DRAWINGS

Example embodiments of the invention are explained in more detail below with the aid of the drawings, in which, in schematic and simplified illustrations in each case.

Identically acting parts are provided in the figures with identical reference symbols.

DETAILED DESCRIPTION OF THE EXAMPLE EMBODIMENTS

Figure 1:
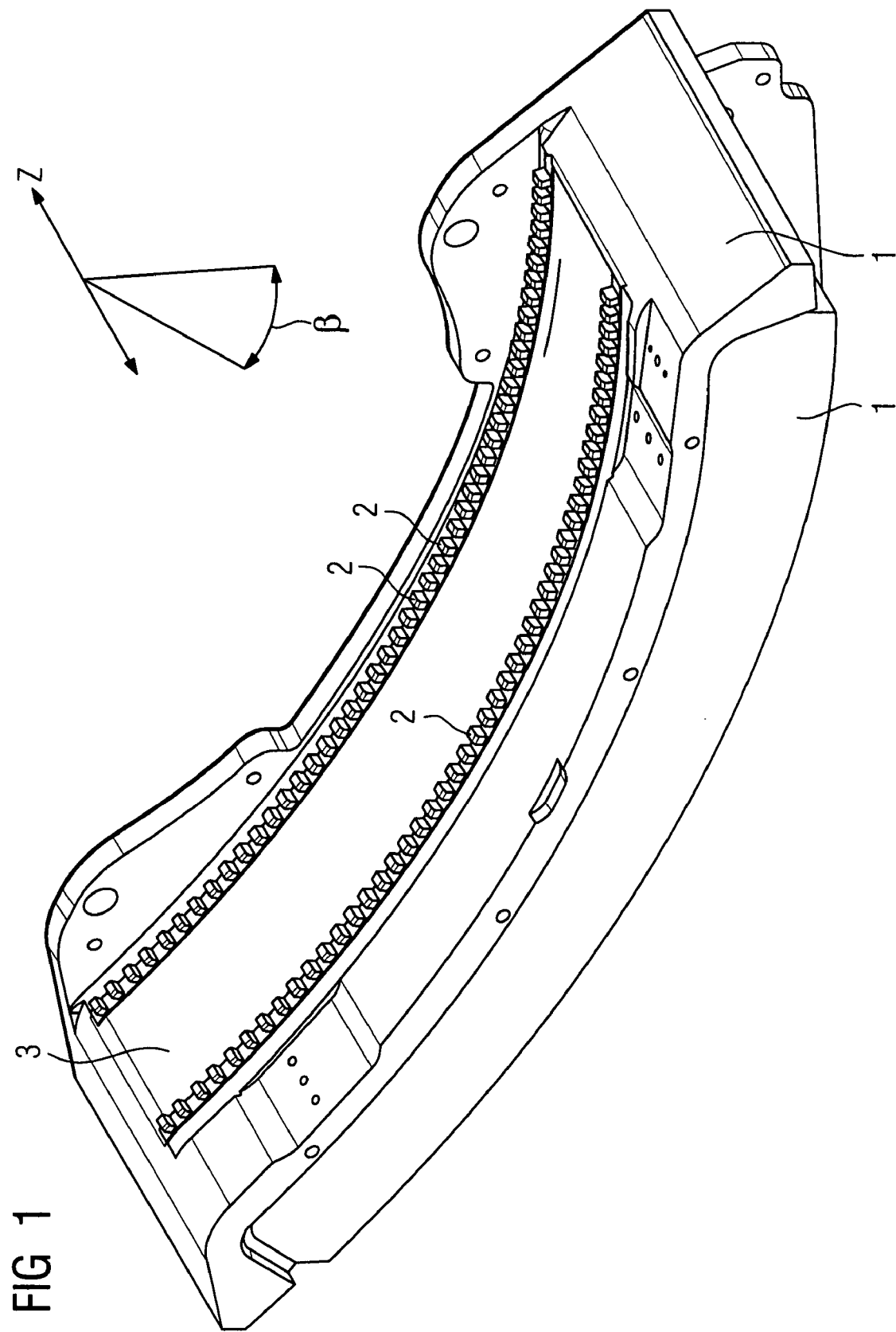
FIG. 1 shows a perspective illustration of a radiation detection unit.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described. Like numbers refer to like elements throughout. As used herein, the term "and/or" includes any and all combinations of one or more of the associated listed items.

An example embodiment of a radiation detection unit 1, as shown in FIG. 1, has individual scattered radiation sensors 2 that are arranged in the form of strips and are arranged in the z-direction on both sides outside the primary fan beam, in order to measure the scattered radiation occurring there. In this example embodiment, the scattered radiation sensors 2 are arranged to this end on both sides of a radiation entry window 3 for the primary radiation. To this end, the scattered radiation sensors 2 are seated on a strip-shaped circuit board (not illustrated) at defined spacings in the β direction (spacing=module pitch, for example), and this is shown more accurately in FIG. 2.

Figure 2:
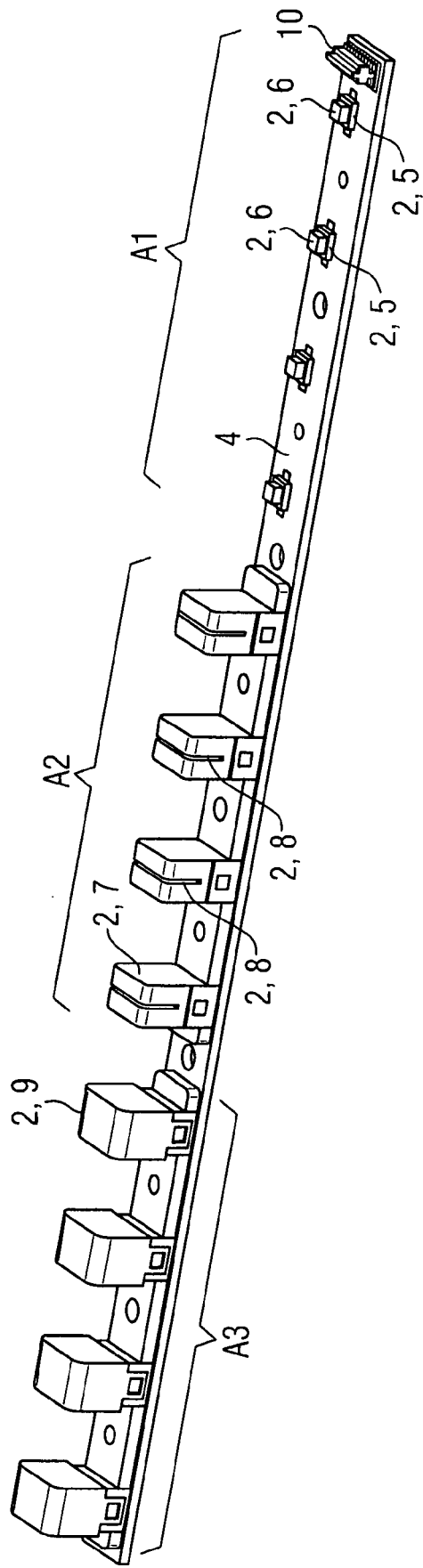
FIG. 2 shows a perspective illustration of a circuit board of the radiation detection unit from FIG. 1, with first scattered radiation sensors.

FIG. 2 shows a circuit board 4 that is used in FIG. 1 and on which scattered radiation sensors 2 are shown in different states of assembly. The group of four A1 scattered radiation sensors 2 arranged on the right shows these without housing and with photodiodes 5 to which scintillator ceramics 6 are applied.

The group of four A2 of scattered radiation sensors 2 that is arranged in the middle is additionally covered with a common sensor housing 7 which is produced completely from radiation absorbing material, that is to say mostly from X-ray absorbing material. The sensor housing 7 has beam entry slits 8 for scattered beam collimation. The sensor housing 7 is produced favorably in terms of cost and mounting using an injection molding method, for example from PA filled with tungsten powder.

In order to eliminate any possible incidents of light in the beam entry slits 8, in the case of the group of four A3 of scattered radiation sensors 2 arranged on the left sealing hoods 9 (made from plastic dyed black, for example) opaque to light are arranged over the corresponding housing parts. Scattered X-radiation penetrating via the slit 8 is converted in the scintillator 6 into light and subsequently into an equivalent current in the photodiode 5. The requisite accuracy of the slit width is produced by a highly accurate web in the injection mold (not shown).

The circuit board 4 further has a plug-in connector 10 for tapping sensor signals of the scattered radiation sensors 2, and passing them onto an appropriate electronic evaluation system.

Figure 3:
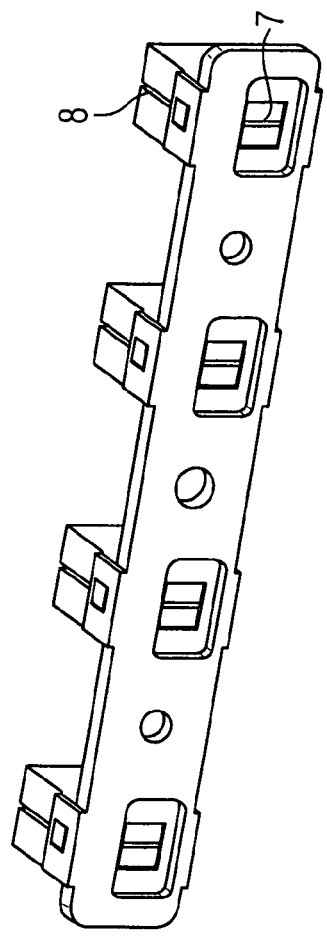
FIG. 3 shows a perspective illustration of an underside of a sensor module with first scattered radiation sensors according to FIG. 2.

FIG. 3 shows the sensor housing 7 from FIG. 2 from the underside, the beam entry slits 8 continuing to be visible.

Figure 4:
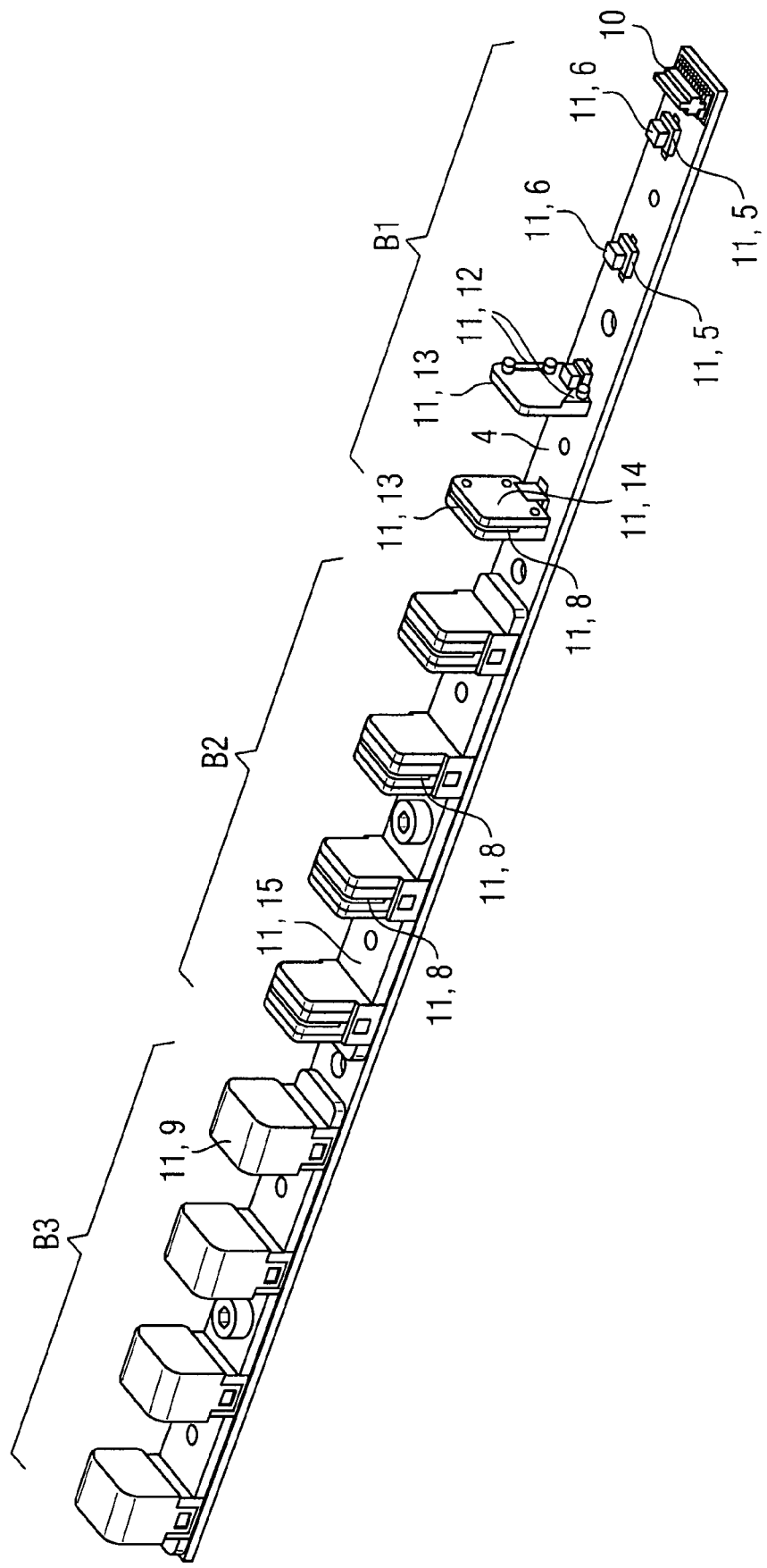
FIG. 4 shows a perspective illustration of a circuit board of the radiation detection unit from FIG. 1, with second scattered radiation sensors.

FIG. 4 shows the circuit board 4 with a further embodiment of scattered radiation sensors 11 in different states of assembly. With the aid of two right-hand elements, the group of four B1 scattered radiation sensors 11 that is arranged on the right-hand side exhibits these in a way similar to the group of four A1 arranged on the right in FIG. 1 without housing, with photodiodes 5 to which scintillator ceramics 6 are applied.

The third scattered radiation sensor 11 from the right-hand side of the group of four B1 has, furthermore, to this end a first shielding plate 13 equipped with spacer webs 12. The fourth scattered radiation sensor 11 from the right of the group of four B1 further has a second shielding plate 14. The beam entry slit 8 is defined to the required accuracy by way of the highly precise spacer webs 12.

The absorbing shielding plates 13, 14 are produced using the injection molding method, for example from PA filled with tungsten powder.

The group of four B2 of scattered radiation sensors 2 arranged in the middle is additionally mounted in a common sensor housing 15.

In a way similar to FIG. 2, in the case of the group of four A3 of scattered radiation sensors 11 arranged on the left, sealing hoods 9 made from plastic dyed black that are opaque to light are arranged over the corresponding housing parts 13, 14, 15. The circuit board 4 also has here a plug-in connector 10 for tapping sensor signals.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A radiation detection unit for a computer tomograph, comprising:
  at least one scattered radiation sensor, set up and arranged to measure scattered radiation, wherein the at least one scattered radiation sensor includes at least one beam entry slit for introducing the secondary radiation, the beam entry slit is formed at least partially by sensor housing parts having radiation absorbing material and the housing parts are produced by injection molding.

2. The radiation detection unit as claimed in claim 1, wherein the at least one scattered radiation sensor is arranged outside a primary fan beam path.

3. The radiation detection unit as claimed in claim 2, wherein the at least one scattered radiation sensor includes a plurality of scattered radiation sensors.

4. The radiation detection unit as claimed in claim 1, wherein the at least one scattered radiation sensor includes a plurality of scattered radiation sensors.

5. The radiation detection unit as claimed in claim 4, wherein the plurality of scattered radiation sensors are arranged in two rows in relation to a gantry rotational axis on both sides of a primary fan beam path.

6. The radiation detection unit as claimed in claim 5, wherein the scattered radiation sensors of a row are arranged at defined spacings from one another.

7. The radiation detection unit as claimed in claim 5, wherein the scattered radiation sensors of a row are arranged at the spacing of a module pitch.

8. A computer tomograph, comprising:
 a plurality of radiation detection units as claimed in claim 4; and
 an evaluation unit to use measured values, output by the at least one scattered radiation sensor, for scattered radiation correction during image calculation.

9. The radiation detection unit as claimed in claim 4, wherein the plurality of scattered radiation sensors each include a photodiode to which scintillation ceramic has been applied.

10. The radiation detection unit as claimed in claim 4, wherein the plurality of scattered radiation sensors each include at least one beam entry slit for introducing the secondary radiation.

11. The radiation detection unit as claimed in claim 10, wherein the beam entry slit is formed at least partially by housing parts having radiation absorbing material.

12. The radiation detection unit as claimed in claim 11, wherein the housing parts include insertion parts made from radiation absorbing material.

13. The radiation detection unit as claimed in claim 11, wherein the housing parts are produced by injection molding.

14. The radiation detection unit as claimed in claim 4, wherein each of the radiation sensors includes a scintillation ceramic.

15. The radiation detection unit as claimed in claim 1, wherein the at least one scattered radiation sensor includes a photodiode to which scintillation ceramic has been applied.

16. The radiation detection unit as claimed in claim 1, wherein the housing parts consist entirely of radiation absorbing material.

17. The radiation detection unit as claimed in claim 1, wherein the housing parts include insertion parts made from radiation absorbing material.

18. A computer tomograph, comprising:
 at least one radiation detection unit as claimed in claim 1; and
 an evaluation unit to use measured values, output by the at least one scattered radiation sensor, for scattered radiation correction during image calculation.

19. the radiation detection unit as claimed in claim 1, wherein the slit is formed in a sensor housing.

20. The radiation detection unit as claimed in claim 19, further including a sealing hood covering the sensor housing.

\* \* \* \* \*